US012062420B2

(12) United States Patent
McNair et al.

(10) Patent No.: US 12,062,420 B2
(45) Date of Patent: *Aug. 13, 2024

(54) SYSTEM AND METHOD FOR RECORD LINKAGE

(71) Applicant: CERNER INNOVATION, INC., Redwood Shores, CA (US)

(72) Inventors: Douglas S. McNair, Seattle, WA (US); Kanakasabha Kailasam, Olathe, KS (US); John Christopher Murrish, Overland Park, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/359,777

(22) Filed: Jul. 26, 2023

(65) Prior Publication Data

US 2023/0386627 A1 Nov. 30, 2023

Related U.S. Application Data

(63) Continuation of application No. 17/740,751, filed on May 10, 2022, now Pat. No. 11,749,388, which is a
(Continued)

(51) Int. Cl.
*G16H 10/60* (2018.01)
*G16H 80/00* (2018.01)

(52) U.S. Cl.
CPC ............ *G16H 10/60* (2018.01); *G16H 80/00* (2018.01)

(58) Field of Classification Search
CPC ........ G06Q 10/00; G06Q 10/60; G06Q 50/22; G06Q 50/24; G06F 19/00; G06F 19/30;
(Continued)

(56) References Cited

U.S. PATENT DOCUMENTS 4,839,853 A 6/1989 Deerwester et al.
5,243,565 A 9/1993 Yamamoto
(Continued)

FOREIGN PATENT DOCUMENTS

EP 1043666 A2 10/2000
EP 2365456 A2 9/2011
(Continued)

OTHER PUBLICATIONS

Abbott et al., "Sequence Analysis and Optimal Matching Methods in Sociology, Review and Prospect", Sociol Meth Res., vol. 29, 2000, pp. 3-33.
(Continued)

*Primary Examiner* — Jason S Tiedeman
(74) *Attorney, Agent, or Firm* — Mughal Gaudry & Franklin PC

(57) ABSTRACT

Methods, systems, and computer-readable media are provided for facilitating record matching and entity resolution and for enabling improvements in record linkage. A power-spectrum-based temporal pattern-specific weight may be incorporated into record linkage methods to enhance the record linkage accuracy and statistical performance. For example, in embodiments, a value-specific weight may be calculated from a population-based frequency of field-specific values and provides an opportunity to capture and measure the relative importance of specific values found in a field. A timeseries-derived Bayesian power spectrum weight may be calculated from the population-based frequency of temporal pattern-specific values in terms of intensities at various frequencies of the power spectrum computed from the timeseries, and further provides an opportunity to capture and measure the relative importance of specific sequences of care episodes.

20 Claims, 6 Drawing Sheets

Related U.S. Application Data continuation of application No. 16/793,870, filed on Feb. 18, 2020, now Pat. No. 11,361,851, which is a continuation of application No. 16/237,206, filed on Dec. 31, 2018, now Pat. No. 10,580,524, which is a continuation of application No. 13/874,961, filed on May 1, 2013, now Pat. No. 10,249,385.

(60) Provisional application No. 61/641,097, filed on May 1, 2012.

(58) Field of Classification Search
CPC ........ G06F 19/34; G06F 19/345; G06F 19/02; G06F 19/36; G06F 16/00; G06F 16/10; G06F 16/20; G06F 16/22; G06F 16/2228; G06F 16/2237; G06F 16/23; G06F 16/2365; G06F 16/30; G06F 16/31; G06F 16/35; G06F 16/38; G06F 16/383; G16H 10/00; G16H 10/60; G16H 15/00; G16H 50/00; G16H 50/70
USPC .......................................................... 705/2, 3
See application file for complete search history.

(56) References Cited

U.S. PATENT DOCUMENTS

| | | |
|---|---|---|
| 5,301,109 A | 4/1994 | Landauer et al. |
| 5,664,109 A | 9/1997 | Johnson et al. |
| 5,809,494 A | 9/1998 | Nguyen |
| 5,835,900 A | 11/1998 | Fagg, III et al. |
| 6,039,688 A | 3/2000 | Douglas et al. |
| 6,122,628 A | 9/2000 | Castelli et al. |
| 6,246,964 B1 | 6/2001 | Blaunstein |
| 6,246,975 B1 | 6/2001 | Rivonelli et al. |
| 6,247,004 B1 | 6/2001 | Moukheibir |
| 6,397,224 B1 | 5/2002 | Zubeldia et al. |
| 6,618,715 B1 | 9/2003 | Johnson et al. |
| 6,654,740 B2 | 11/2003 | Tokuda et al. |
| 6,665,669 B2 | 12/2003 | Han et al. |
| 6,915,254 B1 | 7/2005 | Heinze et al. |
| 6,996,575 B2 | 2/2006 | Cox et al. |
| 7,039,634 B2 | 5/2006 | Xu et al. |
| 7,120,626 B2 | 10/2006 | Li et al. |
| 7,249,117 B2 | 7/2007 | Estes |
| 7,386,522 B1 | 6/2008 | Bigus et al. |
| 7,440,947 B2 | 10/2008 | Adcock et al. |
| 7,447,643 B1 | 11/2008 | Olson et al. |
| 7,496,561 B2 | 2/2009 | Caudill et al. |
| 7,529,765 B2 | 5/2009 | Brants et al. |
| 7,555,425 B2 | 6/2009 | Oon |
| 7,558,778 B2 | 7/2009 | Carus et al. |
| 7,617,078 B2 | 11/2009 | Rao et al. |
| 7,640,171 B2 | 12/2009 | Gendron et al. |
| 7,657,540 B1 | 2/2010 | Bayliss |
| 7,668,820 B2 | 2/2010 | Zuleba |
| 7,720,846 B1 | 5/2010 | Bayliss |
| 7,831,423 B2 | 11/2010 | Schubert |
| 7,844,449 B2 | 11/2010 | Lin et al. |
| 7,844,566 B2 | 11/2010 | Wnek |
| 7,853,456 B2 | 12/2010 | Soto et al. |
| 7,865,373 B2 | 1/2011 | Punzak et al. |
| 7,899,764 B2 | 3/2011 | Martin et al. |
| 7,899,796 B1 | 3/2011 | Borthwick et al. |
| 7,900,052 B2 | 3/2011 | Jonas |
| 7,912,842 B1 | 3/2011 | Bayliss |
| 7,933,909 B2 | 4/2011 | Trepetin |
| 7,953,685 B2 | 5/2011 | Liu et al. |
| 8,015,136 B1 | 9/2011 | Baker et al. |
| 8,078,554 B2 | 12/2011 | Fung et al. |
| 8,126,736 B2 | 2/2012 | Anderson et al. |
| 8,160,895 B2 | 4/2012 | Schmitt et al. |
| 8,165,893 B1 | 4/2012 | Goldberg et al. |
| 8,200,505 B2 | 6/2012 | Walker et al. |
| 8,515,777 B1 | 8/2013 | Rajasenan |
| 8,539,424 B2 | 9/2013 | Tetelbaum |
| 8,589,424 B1 | 11/2013 | Patel et al. |
| 8,666,785 B2 | 3/2014 | Baluta et al. |
| 8,838,628 B2 | 9/2014 | Leighton et al. |
| 8,856,156 B1 | 10/2014 | McNair et al. |
| 8,930,218 B1* | 1/2015 | Oakley .................. G16H 50/20 705/3 |
| 9,375,142 B2 | 6/2016 | Schultz et al. |
| 9,542,647 B1 | 1/2017 | Mirhaji |
| 9,734,146 B1 | 8/2017 | McNair et al. |
| 10,249,385 B1 | 4/2019 | McNair et al. |
| 10,268,687 B1 | 4/2019 | McNair et al. |
| 10,431,336 B1 | 10/2019 | Murrish et al. |
| 10,446,273 B1 | 10/2019 | McNair et al. |
| 10,580,524 B1 | 3/2020 | McNair et al. |
| 10,628,553 B1 | 4/2020 | Murrish et al. |
| 10,769,241 B1 | 9/2020 | McNair |
| 10,854,334 B1 | 12/2020 | McNair et al. |
| 10,946,311 B1 | 3/2021 | McNair |
| 10,957,449 B1 | 3/2021 | McNair et al. |
| 11,100,933 B2 | 8/2021 | Lefkofsky et al. |
| 2002/0007284 A1 | 1/2002 | Schurenberg et al. |
| 2002/0023067 A1 | 2/2002 | Garland et al. |
| 2002/0032583 A1 | 3/2002 | Joao |
| 2002/0035486 A1 | 3/2002 | Huyn et al. |
| 2002/0038227 A1 | 3/2002 | Fey et al. |
| 2002/0038308 A1 | 3/2002 | Cappi |
| 2002/0042793 A1 | 4/2002 | Choi |
| 2002/0073138 A1 | 6/2002 | Gilbert et al. |
| 2002/0128860 A1 | 9/2002 | Leveque et al. |
| 2003/0023571 A1 | 1/2003 | Barnhill |
| 2003/0038308 A1 | 2/2003 | Kim |
| 2003/0046280 A1 | 3/2003 | Rotter et al. |
| 2003/0055679 A1 | 3/2003 | Soll et al. |
| 2003/0163057 A1 | 8/2003 | Flick et al. |
| 2003/0212580 A1 | 11/2003 | Shen |
| 2004/0064438 A1* | 4/2004 | Kostoff .................. G06F 16/35 |
| 2004/0199332 A1 | 10/2004 | Iliff |
| 2004/0230105 A1 | 11/2004 | Geva et al. |
| 2004/0260666 A1 | 12/2004 | Pestotnik et al. |
| 2005/0027562 A1 | 2/2005 | Brown |
| 2005/0049497 A1 | 3/2005 | Krishnan et al. |
| 2005/0055246 A1 | 3/2005 | Simon |
| 2005/0119534 A1 | 6/2005 | Trost et al. |
| 2005/0144042 A1 | 6/2005 | Joffe et al. |
| 2005/0256740 A1 | 11/2005 | Kohan et al. |
| 2005/0272984 A1 | 12/2005 | Huiku |
| 2005/0288910 A1 | 12/2005 | Schlessinger et al. |
| 2006/0020465 A1 | 1/2006 | Cousineau et al. |
| 2006/0036619 A1 | 2/2006 | Fuerst et al. |
| 2006/0064447 A1 | 3/2006 | Malkov |
| 2006/0074824 A1 | 4/2006 | Li |
| 2006/0129427 A1 | 6/2006 | Wennberg |
| 2006/0161457 A1 | 7/2006 | Rapaport et al. |
| 2006/0173663 A1 | 8/2006 | Langheier et al. |
| 2006/0179050 A1* | 8/2006 | Giang .................. G06F 16/3346 707/999.005 |
| 2006/0205564 A1 | 9/2006 | Peterson |
| 2006/0206027 A1 | 9/2006 | Malone |
| 2006/0206359 A1 | 9/2006 | Stang |
| 2006/0218010 A1 | 9/2006 | Michon et al. |
| 2006/0265253 A1 | 11/2006 | Rao et al. |
| 2006/0271556 A1 | 11/2006 | Mukherjee et al. |
| 2007/0005621 A1 | 1/2007 | Lesh et al. |
| 2007/0026365 A1 | 2/2007 | Friedrich et al. |
| 2007/0031873 A1 | 2/2007 | Wang et al. |
| 2007/0094048 A1 | 4/2007 | Grichnik |
| 2007/0106533 A1 | 5/2007 | Greene |
| 2007/0106752 A1 | 5/2007 | Moore |
| 2007/0233391 A1 | 10/2007 | Milstein et al. |
| 2007/0239482 A1 | 10/2007 | Finn et al. |
| 2007/0244724 A1 | 10/2007 | Pendergast et al. |
| 2008/0021288 A1 | 1/2008 | Bowman et al. |
| 2008/0046292 A1 | 2/2008 | Myers et al. |
| 2008/0097938 A1 | 4/2008 | Guyon et al. |
| 2008/0131374 A1 | 6/2008 | Medich et al. |
| 2008/0133269 A1 | 6/2008 | Ching |
| 2008/0147438 A1 | 6/2008 | Kil |
| 2008/0147441 A1 | 6/2008 | Kil |

(56) References Cited

U.S. PATENT DOCUMENTS

| | | |
|---|---|---|
| 2008/0172214 A1 | 7/2008 | Col et al. |
| 2008/0172251 A1 | 7/2008 | Reichert et al. |
| 2008/0183454 A1 | 7/2008 | Barabasi et al. |
| 2008/0195422 A1 | 8/2008 | Nessinger et al. |
| 2008/0243548 A1 | 10/2008 | Cafer |
| 2008/0249376 A1 | 10/2008 | Zaleski |
| 2008/0255884 A1 | 10/2008 | Carus et al. |
| 2008/0256006 A1 | 10/2008 | Buscema et al. |
| 2008/0268413 A1 | 10/2008 | Leichner |
| 2008/0275731 A1 | 11/2008 | Rao et al. |
| 2008/0287746 A1 | 11/2008 | Reisman |
| 2008/0288292 A1 | 11/2008 | Bi et al. |
| 2008/0288474 A1 | 11/2008 | Chin et al. |
| 2008/0294692 A1 | 11/2008 | Angell et al. |
| 2008/0301177 A1 | 12/2008 | Doherty |
| 2008/0306926 A1 | 12/2008 | Friedlander et al. |
| 2009/0006431 A1 | 1/2009 | Agrawal et al. |
| 2009/0012928 A1 | 1/2009 | Lussier et al. |
| 2009/0112892 A1 | 4/2009 | Cardie et al. |
| 2009/0125333 A1 | 5/2009 | Heywood et al. |
| 2009/0132284 A1 | 5/2009 | Fey et al. |
| 2009/0164249 A1 | 6/2009 | Hunt et al. |
| 2009/0228303 A1 | 9/2009 | Faulkner et al. |
| 2009/0259493 A1 | 10/2009 | Venon et al. |
| 2009/0299767 A1 | 12/2009 | Michon et al. |
| 2009/0304246 A1 | 12/2009 | Walker et al. |
| 2009/0313041 A1 | 12/2009 | Eder |
| 2009/0318775 A1 | 12/2009 | Michelson et al. |
| 2009/0319295 A1 | 12/2009 | Kass-Hout et al. |
| 2010/0082369 A1 | 4/2010 | Prenelus et al. |
| 2010/0088117 A1 | 4/2010 | Belden et al. |
| 2010/0121883 A1 | 5/2010 | Cutting et al. |
| 2010/0131434 A1 | 5/2010 | Magent et al. |
| 2010/0131438 A1 | 5/2010 | Pandya et al. |
| 2010/0131482 A1 | 5/2010 | Linthicum et al. |
| 2010/0131883 A1 | 5/2010 | Linthicum et al. |
| 2010/0142774 A1 | 6/2010 | Ben-Haim et al. |
| 2010/0145720 A1 | 6/2010 | Reiner |
| 2010/0153133 A1 | 6/2010 | Angell et al. |
| 2010/0179818 A1 | 7/2010 | Kelly et al. |
| 2010/0185685 A1 | 7/2010 | Chew et al. |
| 2010/0198755 A1 | 8/2010 | Soll et al. |
| 2010/0235330 A1 | 9/2010 | Reiner |
| 2010/0274576 A1 | 10/2010 | Young |
| 2010/0293003 A1 | 11/2010 | Abbo |
| 2010/0299155 A1 | 11/2010 | Findlay et al. |
| 2010/0324938 A1 | 12/2010 | Ennett et al. |
| 2011/0010401 A1 | 1/2011 | Adams et al. |
| 2011/0015937 A1 | 1/2011 | Janas, III et al. |
| 2011/0046979 A1 | 2/2011 | Tulipano et al. |
| 2011/0067108 A1 | 3/2011 | Hoglund |
| 2011/0077973 A1 | 3/2011 | Breitenstein et al. |
| 2011/0087501 A1 | 4/2011 | Severin |
| 2011/0093467 A1 | 4/2011 | Sharp et al. |
| 2011/0119089 A1 | 5/2011 | Carlisle |
| 2011/0161110 A1 | 6/2011 | Mault |
| 2011/0201900 A1 | 8/2011 | Zhang et al. |
| 2011/0225001 A1 | 9/2011 | Shen |
| 2011/0246238 A1 | 10/2011 | Vdovjak et al. |
| 2011/0270629 A1 | 11/2011 | Abbo |
| 2011/0295621 A1 | 12/2011 | Farooq et al. |
| 2011/0306845 A1 | 12/2011 | Osorio |
| 2012/0016685 A1 | 1/2012 | Ryan et al. |
| 2012/0020536 A1 | 1/2012 | Moehrle |
| 2012/0047105 A1 | 2/2012 | Saigal et al. |
| 2012/0059779 A1 | 3/2012 | Syed et al. |
| 2012/0072235 A1 | 3/2012 | Varadarajan et al. |
| 2012/0078127 A1 | 3/2012 | McDonald et al. |
| 2012/0086963 A1 | 4/2012 | Fujitsuka et al. |
| 2012/0089420 A1 | 4/2012 | Hoffman et al. |
| 2012/0089421 A1 | 4/2012 | Hoffman et al. |
| 2012/0109685 A1 | 5/2012 | Carter et al. |
| 2012/0110016 A1 | 5/2012 | Phillips |
| 2012/0173475 A1 | 7/2012 | Ash et al. |
| 2012/0174014 A1 | 7/2012 | Ash et al. |
| 2012/0174018 A1 | 7/2012 | Ash et al. |
| 2012/0175475 A1 | 7/2012 | McErlane |
| 2012/0185275 A1 | 7/2012 | Loghmani |
| 2012/0203575 A1 | 8/2012 | Tulipano et al. |
| 2012/0203576 A1 | 8/2012 | Bucur et al. |
| 2012/0215784 A1 | 8/2012 | King et al. |
| 2012/0232930 A1 | 9/2012 | Schmidt et al. |
| 2013/0006911 A1 | 1/2013 | Christie, IV et al. |
| 2013/0023434 A1 | 1/2013 | Laar |
| 2013/0031613 A1 | 1/2013 | Shanabrook et al. |
| 2013/0046529 A1 | 2/2013 | Grain et al. |
| 2013/0046558 A1 | 2/2013 | Landi et al. |
| 2013/0080192 A1 | 3/2013 | Bucur et al. |
| 2013/0110547 A1 | 5/2013 | Englund et al. |
| 2013/0110548 A1 | 5/2013 | Kutty |
| 2013/0132308 A1 | 5/2013 | Boss et al. |
| 2013/0132312 A1 | 5/2013 | Lee et al. |
| 2013/0132323 A1 | 5/2013 | Soto et al. |
| 2013/0158968 A1 | 6/2013 | Ash et al. |
| 2013/0197938 A1 | 8/2013 | Bayouk et al. |
| 2013/0245389 A1 | 9/2013 | Schultz et al. |
| 2014/0081652 A1 | 3/2014 | Klindworth |
| 2014/0095184 A1 | 4/2014 | Gotz et al. |
| 2014/0095186 A1 | 4/2014 | Gotz et al. |
| 2014/0180699 A1 | 6/2014 | Massa et al. |
| 2014/0181128 A1 | 6/2014 | Riskin et al. |
| 2014/0200414 A1 | 7/2014 | Osorio |
| 2014/0336539 A1 | 11/2014 | Torres et al. |
| 2015/0049947 A1 | 2/2015 | Katsaros et al. |
| 2015/0161329 A1 | 6/2015 | Mabotuwana et al. |
| 2015/0193583 A1 | 7/2015 | McNair et al. |
| 2015/0254408 A1 | 9/2015 | Mahtani et al. |
| 2015/0324535 A1 | 11/2015 | Ash et al. |
| 2015/0363559 A1 | 12/2015 | Jackson et al. |
| 2016/0004840 A1 | 1/2016 | Rust et al. |
| 2016/0063212 A1 | 3/2016 | Monier et al. |
| 2016/0143594 A1 | 5/2016 | Moorman et al. |
| 2017/0098358 A1 | 4/2017 | Bechtel et al. |
| 2017/0124269 A1 | 5/2017 | McNair et al. |
| 2019/0336085 A1 | 11/2019 | Kayser et al. |
| 2020/0335179 A1 | 10/2020 | Stojadinovic et al. |
| 2021/0177338 A1 | 6/2021 | Pagi et al. |

FOREIGN PATENT DOCUMENTS

| | | |
|---|---|---|
| WO | 2006002465 A1 | 1/2006 |
| WO | 2009112977 A1 | 9/2009 |
| WO | 2010045463 A2 | 4/2010 |
| WO | 2012122122 A1 | 9/2012 |
| WO | 2012122195 A1 | 9/2012 |
| WO | 2012122196 A2 | 9/2012 |

OTHER PUBLICATIONS

Abernethy et al., "Eliciting Consumer Preferences Using Robust Adaptive Choice Questionnaires", IEEE Transactions on Knowledge and Data Engineering, vol. 20, No. 2, Feb. 2008, pp. 145-155.

Agrawal et al., "Fast Discovery of Association Rules", Advances in Knowledge Discovery and Data Mining, Menlo Park, AAAI Press, 1996, pp. 307-328.

Appavoo et al., "Enabling Automomic Behavior in Systems Software with Hot Swapping", IBM Systems Journal, vol. 42, No. 1, 2003, pp. 60-76.

Aronson, Alan R., "MetaMap: Mapping Text to the UMLS Metathesaurus", 2006, 26 pages.

Arpaia et al., "Multi-Agent Remote Predictive Diagnosis of Dangerous Good Transports", Instrumentation and Measurement Technology Conference, Proceedings of the IEEE, May 17-19, 2005, pp. 1685-1690.

Berchtold et al., "The Mixture Transition Distribution Model for High-Order Markov Chains and Non-Gaussian Time Series", Statistical Science, vol. 17, No. 3, 2002, pp. 328-356.

Berry et al., "Care Coordination for Patients with Complex Health Profiles in Inpatient and Outpatient Settings", Mayo Clinic Proceedings, available online at www.mayclinicproceedings.org., 2013, pp. 1-11.

(56) References Cited

OTHER PUBLICATIONS

Billari et al., "Timing, Sequencing, and Quantum of Life Course Events: A Machine-Learning Approach", European Journal of Population, vol. 22, 2006, pp. 37-65.
Cohen et al., "Integrated Complex Care Coordination For Children with Medical Complexity: A Mixed-Methods Evaluation of Tertiary Care-Community Collaboration", BMC Health Services Research, vol. 12, No. 366, Oct. 23, 2012, 23 pages.
Cook et al., "Making Prophecies with Decision Predicates", ACM 978-14503-0490-0/11/01, Jan. 2011, 14 pages.
Deville et al., "Correspondence Analysis with an Extension Towards Nominal Time Series", Journal of Econometrics, vol. 22, 1983, pp. 169-189.
Dijkstra et al., "Measuring the Agreement Between Sequences", Sociological Methods and Research, vol. 24, No. 2, Nov. 1995, pp. 214-231.
Duff, I., "Development and history of sparse direct methods", SIAM Conference on Applied Linear Algebra, available online at http://www.numerical.rl.ac.uk/people/isd/isd.html, Oct. 26-29, 2009, 44 pages.
Dvorak et al., "Football injuries and Physical Symptoms: A Review of the Literature", The American Journal of Sports Medicine, vol. 28, No. 5, 2000, pp. S3-S9.
Dvorak et al., "Risk Factor Analysis for Injuries in Football Players: Possibilities for a Prevention Program", The American Journal of Sport Medicine, vol. 28, No. 5, 2000, pp. S69-S74.
Final Office Action for U.S. Appl. No. 16/717,299, mailed Oct. 27, 2022, 13 pages.
Final Office Action for U.S. Appl. No. 16/819,890 mailed on Oct. 27, 2022, 17 pages.
Final Office Action for U.S. Appl. No. 17/011,474, mailed Oct. 12, 2022, 17 pages.
First Action Interview Office Action received for U.S. Appl. No. 16/714,221, mailed on Apr. 4, 2022, 19 pages.
Han et al., "Frequent Pattern Mining: Current status and future directions", Data Mining and Knowledge Discovery, vol. 15, 2007, pp. 55-86.
Hawkins et al., "A Prospective Eidemiological Study of Injuries in Four English Professional Football Clubs", Br J Sports Med., vol. 33, 1999, 196-203.
Huyse et al., "Compri—An Instrument to Detect Patients with Complex Care Needs", Psychosomatics, vol. 42, No. 3, May-Jun. 2001, 7 pages.
John et al, "Neuro-Fuzzy Clustering of Radiographic Tibia Image Data Using Type 2 Fuzzy Sets", Information Sciences, vol. 125, issues 1-4, 2000, ISSN 0020-0255, available online at https://www.sciencedirect.com/science/article/pii/S002002550000009, 2000, pp. 65-82.
Junge et al., "Soccer Injuries: A Review on Incidence and Prevention", Sports Med., vol. 34, 2004, pp. 929-938.
Kang et al., "Mining Based Decision Support Multi-agent System for Personalized e-Healthcare Service", Proceedings of the 2nd KES International conference on Agent and multi-agent systems: technologies and applications, 2008, pp. 733-742.
Kiran et al., "An Improved Multiple Minimum Support Based Approach to Mine Rare Association Rules", Proceedings of the IEEE Symposium on Computational Intelligence and Data Mining, 2009, 8 pages.
Mabry et al., "Clinical Decision Support with IM-Agents and ERMA Multi-agents", Department of Computer Science and Emergency Medicine, 2004, 6 pages.
Nealon et al., "Agent-Based Applications in Health Care", Applications of Software Agent Technology in the Health Care Domain, 2003, pp. 1-17.
Nielsen et al., "Epidemiology and Traumatology of Injuries in Soccer", Am J Sports Med., vol. 17, 1989, pp. 803-807.
Non-Final Office Action received for U.S. Appl. No. 16/717,299, mailed on Apr. 27, 2022, 10 pages.
Non-Final Office Action received for U.S. Appl. No. 16/819,890, mailed on Apr. 28, 2022.
Notice of Allowance for U.S. Appl. No. 14/148,039, dated Jul. 11, 2022, 10 pages.
Notice of Allowance for U.S. Appl. No. 17/387,786 mailed Nov. 30, 2022.
Ohno-Machado, L., "Realizing the full potential of electronic health records: the role of natural language processing", Journal of American Medical Information Association., vol. 18, No. 5, Sep. 2011, p. 539.
Othman et al., "Agent Based Preprocessing", International Conference on Intelligent and Advanced Systems, 2007, pp. 219-223.
Prados-Suarez et al., "Contextualized Access to Electronic Health Records in Cardiology", IEEE Transactions on Information Technology in Biomedicine, vol. 16, No. 3, doi:10.1109/TITB.2011.2178033., May 2012, pp. 401-412.
Roever, C., "Package 'Bayesian Spectral Inference'", r-project.org, Feb. 21, 2013, pp. 1-27.
Sariyar et al., "The RecordLinkage Package: Detecting Errors in Data", The R Journal, vol. 2, No. 2, Dec. 2010, pp. 61-67.
Seibig et al., "Collection of Annotated Data in a Clinical Validation Study for Alarm Algorithms in Intensive Care—A Methodologic Framework", Journal of Critical Care, vol. 25, 2010, pp. 128-135.
Shirabad et al., "Implementating an Integrative Multi-agent Clinical Decision Support System with Open Source Software", Journal of Medical Systems 36, available online at https://doi.org/10.1007/s10916-010-9452-9, 2012, pp. 123-137.
Ta et al., Data Descriptor: Columbia Open Health Data, Clinical Concept Prevalence and Co-occurence from Electronic Health Records, Scientific data, vol. 5, 180273, doi:10.1038/sdata.2018.273, Nov. 27, 2018, pp. 1-17.
The Comprehensive R Archive Network, R, Available online at: http://cran.r-project-org, retrieved on Feb. 27, 2020, 1 page.
Townsend, H., "Natural Language Processing and Clinical Outcomes: The Promise and Progress of NLP for Improved Care", Journal of AHIMA, vol. 84, No. 2, available online at https://bok.ahima.org/doc?oid=106198#XOSgnSgzY2x, Mar. 2013, 3 pages.
Uhrmacher et al., "Distributed, Parallel Simulation of Multiple, Deliberative Agents", Proceedings of the fourteenth workshop on Parallel and distributed simulation, May 2000, pp. 101-108.
Xue et al., "Fast Query by Example of Environment Sounds via Robust and Efficient Cluster-based Indexing", 2008, IEEE International Conference on Acoustics, Speech and Signal Processing, available online at doi:10.1109/ICASSP.2008.4517532, 2008, pp. 5-8.
Zaki, M., "Spade: An Efficient Algorithm for Mining Frequent Sequences", Machine Learning, vol. 42, 2001, pp. 31-60.

\* cited by examiner

| fn_c1 | fn_c2 | ln_c1 | ln_c2 | by | bm | bd | v1 | v2 | v3 | v4 | rl_wt | ps_wt | RMS(rl,ps) |
|---|---|---|---|---|---|---|---|---|---|---|---|---|---|
| MICHAEL | #N/A | MEYER | #N/A | 1988 | 1 | 31 | 225 | 200 | 168 | 187 | 0.8258 | 0.9250 | 0.8768 |
| MICHAEL | #N/A | MYER | #N/A | 1988 | 1 | 31 | 59 | 96 | 122 | 60 | 0.6779 | 0.8250 | 0.7550 |
| MICHAEL | #N/A | MAYER | #N/A | 1988 | 1 | 30 | 51 | 71 | 1 | 1 | 0.5244 | 0.8750 | 0.7213 |
| MICHAEL | #N/A | KUEHN | #N/A | 1943 | 10 | 9 | 3 | 4 | 4 | 3 | 0.1574 | 0.9750 | 0.6984 |
| MICHAEL | #N/A | MEIER | #N/A | 1988 | 1 | 9 | 120 | 152 | 74 | 141 | 0.5244 | 0.7250 | 0.6327 |
| MICHAEL | #N/A | KELLER | #N/A | 1965 | 3 | 19 | 78 | 34 | 115 | 63 | 0.1574 | 0.7750 | 0.5592 |
| MICHAEL | #N/A | VOGEL | #N/A | 1967 | 8 | 26 | 275 | 47 | 260 | 13 | 0.1574 | 0.6750 | 0.4901 |
| MICHAEL | #N/A | SCHAEFER | #N/A | 1991 | 5 | 30 | 301 | 156 | 78 | 172 | 0.1574 | 0.6250 | 0.4557 |
| MICHAEL | #N/A | FISCHER | #N/A | 1951 | 7 | 1 | 39 | 224 | 14 | 307 | 0.1574 | 0.5750 | 0.4215 |
| MICHAEL | #N/A | HAHN | #N/A | 1971 | 2 | 27 | 315 | 209 | 367 | 420 | 0.1574 | 0.5250 | 0.3876 |
| DIETER | #N/A | MEYER | #N/A | 1967 | 6 | 16 | 266 | 467 | 496 | 348 | 0.1479 | 0.4750 | 0.3518 |
| MANFRED | #N/A | MEYER | #N/A | 1959 | 10 | 12 | 328 | 245 | 361 | 91 | 0.1479 | 0.4250 | 0.3182 |
| STEFAN | #N/A | MEYER | #N/A | 1960 | 2 | 23 | 602 | 728 | 301 | 159 | 0.1479 | 0.3750 | 0.2850 |
| KLAUS | #N/A | MEIER | #N/A | 1983 | 11 | 10 | 427 | 242 | 444 | 675 | 0.1479 | 0.3250 | 0.2525 |
| THOMAS | #N/A | MAIER | #N/A | 1941 | 4 | 5 | 364 | 5 | 54 | 1 | 0.1479 | 0.2750 | 0.2208 |
| ANDREAS | #N/A | MAYER | #N/A | 1959 | 12 | 24 | 43 | 206 | 391 | 454 | 0.1479 | 0.2250 | 0.1904 |
| GERHARD | #N/A | MEYER | #N/A | 1941 | 11 | 25 | 465 | 255 | 94 | 14 | 0.1479 | 0.1750 | 0.1620 |
| JUERGEN | #N/A | MEIER | #N/A | 1983 | 7 | 7 | 582 | 370 | 369 | 48 | 0.1479 | 0.1250 | 0.1369 |
| UWE | #N/A | MEIER | #N/A | 1942 | 9 | 20 | 111 | 418 | 727 | 642 | 0.1479 | 0.0750 | 0.1173 |
| CARSTEN | #N/A | MEIER | #N/A | 1949 | 7 | 22 | 29 | 554 | 582 | 531 | 0.1479 | 0.0250 | 0.1061 |

FIG. 3.

SYSTEM AND METHOD FOR RECORD LINKAGE

CROSS-REFERENCE TO RELATED APPLICATIONS

This application is a continuation of U.S. patent application Ser. No. 17/740,751, titled "System and Method For Record Linkage", filed May 10, 2022, which is a continuation of U.S. patent application Ser. No. 16/793,870, titled "System and Method For Record Linkage", filed Feb. 18, 2020, now U.S. Pat. No. 11,361,851, issued on Jun. 14, 2022, which is a continuation of U.S. patent application Ser. No. 16/237,206, titled "System and Method For Record Linkage," filed Dec. 31, 2018, now U.S. Pat. No. 10,580,524, issued on Mar. 3, 2020, which is a continuation of U.S. patent application Ser. No. 13/874,961, titled, "System and Method For Record Linkage," filed May 1, 2013, now U.S. Pat. No. 10,249,385, issued on Apr. 2, 2019, which claims the benefit of U.S. Provisional Application No. 61/641,097, titled "System And Method For Record Linkage," filed May 1, 2012, all of which are hereby expressly incorporated by reference in their entirety.

BACKGROUND

In the practice of administering health care, single patient records may be collected among different health-care systems with each system using patient identifiers that are different from the identifiers used by the other health-care systems. Furthermore, patient records collected within the same health-care institution may use multiple identifiers for referring to the same patient. Still further, typographic errors, which happen routinely in the course of collecting patient information and are unavoidable, can result in inaccurate and inconsistent data about a single patient. In some instances, certain data collected about a patient, such as weight, body-mass-index (BMI), or height, may be falsely reported. For example, a patient might underreport his or her true weight due to reasons of vanity. Ultimately, such inconsistencies lead to incomplete data sharing among health-care professionals, patients, and data repositories.

Record linkage is the methodology of bringing together corresponding records from two or more files or finding duplicates within files. The term record linkage originated in the public health area when files associated with an individual patient were brought together using name, date of birth, and other information. Patient record linkage, or matching, is a key process for identifying and connecting records belonging to the same patient, including records created over extended time periods and across several disparate data sources.

A formal mathematical foundation for record linkage was proposed by Fellegi and Sunter, and uses a field-specific weight that is based on the agreement/disagreement between corresponding fields of data. In the Fellegi-Sunter (F-S) approach, two datasets A and B are matched by way of classifying pairs in a product space A×B from the two datasets A and B into M, a set of true matches, and U, a set of true nonmatches.

To establish the match or nonmatch status of two records, the F-S method produces a composite likelihood ratio that is the sum of field-specific weights for each record-pair. The field-specific weight is based on a likelihood ratio whose numerator is the probability that a matching field agrees given the comparison pair is a true match; its denominator is the probability that a matching field agrees given that comparison pair is a true nonmatch. This ratio reflects the relative importance of a comparison field in predicting match status. For example, agreement on date of birth receives a higher positive weight than agreement on sex, but disagreement on date of birth receives fewer penalties (a smaller negative weight) than sex receives for disagreement. The sum of all field-specific weights produces the composite match score for a pair.

While the F-S method may produce reasonably accurate results, it does not explicitly accommodate the notion of a value-specific weight or otherwise leverage the information contained in field-specific values. As a result, each field receives an identical agreement weight for all record pairs regardless of the relative importance of the specific values being compared for that field. Likewise F-S does not take into account the information that is embodied in a timeseries of records, including for example, the time intervals that separate serial episodes for entities that have experienced two or more episodes of activity that resulted in creating and storing records of the episodes.

Further limitations resulting in the F-S approach and prior attempts to provide record linkage include:
  (1) Excessive false-negative rates, such as false misses or nonlinkages, associated with spelling errors; fat-fingered entries, such as close-on-keyboard entries or replicated keystrokes; transpositions of digits in identifiers; aliases for first names; variable use of middle-name as first-name; deception/fraud involving use of a false name; transpositions of (first) given name and (last) family name; omissions (e.g., don't know or don't enter first or middle name); mishandling of records, for example records within family related to twins/triplets/octuplets/etc.; transpositions in date fields; invalid or out-of-date values, for example insurer/plan have lapsed and/or are no longer in force; missing and/or anonymous data, for example an entry for John or Jane Doe with a SSN of 999-99-9999; omission of area code or zip code; or other causes. In health care, such false-negatives generally lead to errors of omission: failures to implement the best treatment or other action. However, as in the case of allergy-checking or drug-drug interaction checking, false-negatives may also lead to errors of commission: undertaking a course of treatment that is harmful and that could have been interdicted had the true match been identified.
  (2) Excessive false-positive rate (i.e., false linkages). False-positive linkage of entities that are not in fact the same person generally leads to errors of commission: undertaking a course of action that would have been beneficial for one of the entities but that is not beneficial for the other entity.
  (3) Reliance on a higher number of variables to perform matching, which fails to achieve the desired sensitivity and specificity, chiefly because the rate of missingness for the extended-range variables is excessive.

Accordingly, it is therefore desirable to establish systems and methods for providing more accurate and efficient record linkage including using time-oriented information that is readily available for each of the records in the repository and for any new record for which a match in the repository is sought. Such record linkage technology, which is particularly useful when patient records lack any unique identifier, offers numerous benefits to physicians and healthcare organizations, not only by improving the quality of patient care, but also by facilitating clinical research and population-based studies. It is further important for the aggregating and integrating of health information.

SUMMARY

A system, methods and computer-readable media are provided for facilitating record matching and entity resolution and for enabling improvements in record linkage including determining records that refer to the same entity or individual as one or more other records in a collection of records that are stored in a computer system and detecting matches of a new record with one or more others that already exist and are stored in online databases. A power-spectrum-based temporal pattern-specific weight may be incorporated into record linkage methods to enhance the record linkage accuracy and statistical performance. For example, in embodiments, a value-specific weight may be calculated from a population-based frequency of field-specific values and provides an opportunity to capture and measure the relative importance of specific values found in a field. A timeseries-derived Bayesian power spectrum weight may be calculated from the population-based frequency of temporal pattern-specific values in terms of intensities at various frequencies of the power spectrum computed from the timeseries, and further provides an opportunity to capture and measure the relative importance of specific sequences of care episodes.

In embodiments, time series are formed by (a) provisionally appending a proband episode date-time stamp to those records of other episodes for which conventional multivariate evidence exists favoring linkage of the proband to other previously linked episodes, (b) calculating Bayesian power spectra for each such combination, (c) repeatedly randomly sampling the spectra to calculate the median likelihood for each, with for example, Bonferroni or other suitable correction for timeseries length, (d) normalizing the median likelihood values so as to be on a scale that is commensurate with the weights calculated by conventional record-linkage system and method, (e) combining each scaled median likelihood with the corresponding conventional record-linkage weights using, for example, a root-mean-square or dot-product cosine measure or other suitable score, and (f) rank-ordering the resulting set according to the combined score.

In such ways, embodiments of the invention provide advantages including more accurate, dynamic, and robust matching, and matching where limited data exists. Embodiments further offer numerous benefits to physicians and health-care organizations, not only by improving the quality of patient care, but also by facilitating clinical research and population-based studies.

BRIEF DESCRIPTION OF THE DRAWINGS

Embodiments of the invention are described in detail below with reference to the attached drawing figures, wherein:

FIG. 3 depicts example outputs of an embodiment for resolving an entity.

DETAILED DESCRIPTION

Figure 1A:
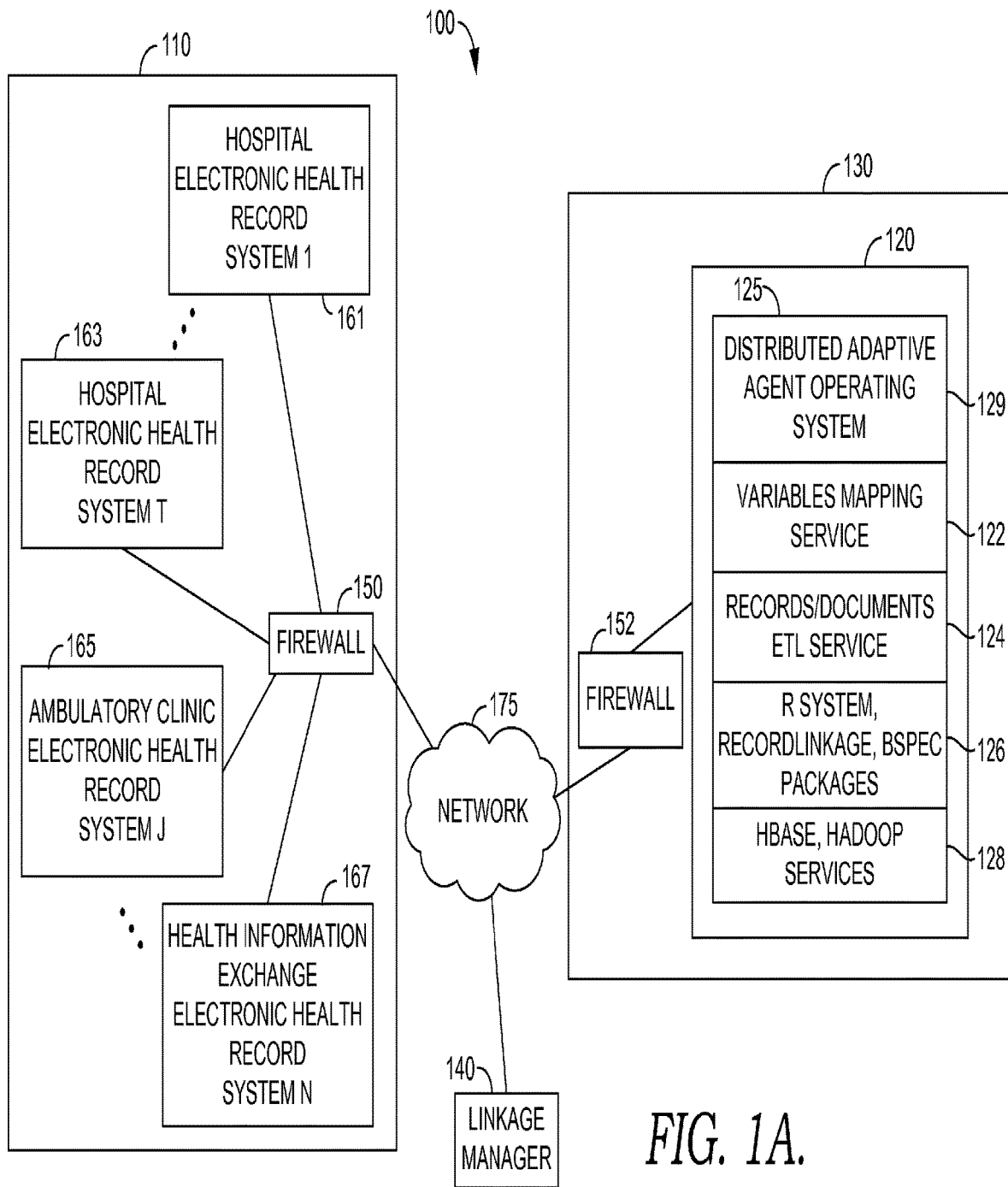
FIGS. 1A, 1B, and 1C depict aspects of an illustrative operating environment suitable for practicing embodiments of the invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things, a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable and nonremovable media, and contemplate media readable by a database, a switch, and various other network devices. By way of example and not limitation, computer-readable media comprise media implemented in any method or technology for storing information, including computer-storage media and communications media. Examples of stored information include computer-useable instructions, data structures, program modules, and other data representations. Computer-readable storage media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

As discussed above, embodiments of the invention are provided for facilitating record matching and entity resolution by incorporating power-spectrum-based temporal pattern-specific weighting into record linkage methods. In some embodiments, health-care-related time series data are used for accurate and efficient record matching, by extracting maximum amounts of information from short time series, which may occur infrequently. For example, a healthy patient may visit the doctor's office only once every several years, thereby resulting in a limited time series of information. By way of analogy, similar challenges are encountered by experimental astrophysicists who study gravitational waves. Out of necessity, these astrophysicists developed techniques that extract the maximum amount of information from short time series that arise from rare, brief events. Similar methodologies used in empirical identification of time series associated with gravitational waves can be fruitfully applied to the problem of identifying other short time series, including time series that arise in health and health-care contexts.

For example, whenever two compact celestial objects, such as white dwarfs, neutron stars, or black holes, are in close orbit, they emit intense gravitational waves. Over time, as the objects spiral closer to each other, the frequency and amplitude of this radiation increases, resulting in a swept-frequency pattern known as a "chirp." Gravitational waves have not yet been directly detected on Earth because of their extremely small effect on matter. But their existence can be inferred from changes in the orbital periods of the objects, for example, changes in the orbital periods of binary pulsars, such as PSR 1913+16. 'Orbital lifetime' is a characteristic property of celestial objects that are sources of gravitational radiation. Orbital lifetime determines the average number of binary stars (i.e., "binaries") in the universe whose gravitational waves are likely to be detectable. Short-lifetime binaries produce strong, readily detectable gravitational radiation but are rare. Long-lifetime binaries, which are more numerous, emit gravitational waves that are weak and hard to detect.

Gravitational radiation detection is facilitated using a class of instruments such as LIGO ("Laser Interferometer Gravitational-Wave Observatory," a ground-based interferometer that comprises multiple observatories, separated over a geographical distance), which is most sensitive in the frequency band (30 Hz to 7 KHz) where two neutron stars are about to merge. The time frame for such a merger or coalescence of the objects lasts only a few seconds. Thus LIGO or similar instruments must detect this "blink" of gravitational waves emitted over a few seconds out of a million-year orbital lifetime. It is calculated that only about once per decade or so does a coalescence of two neutron stars happen in a manner that could be detected by LIGO.

Current gravitational-wave detector design accounts for this very limited duration of data. There are approximately $3\times10^{10}$ msec per year, so even a fluctuation that has a probability of $10^{-10}$ of occurring is likely to occur in one year of data. To eliminate most false-positive signals, a signal-to-noise ratio threshold is used or, in some cases, multi-detector coincidence discrimination. However, concerning record linkage, there is no possibility of coincidence discrimination by multiple events synchronously incident upon two or more 'detectors'. Each event is incident upon only one facility. Therefore, some embodiments of the invention, which utilize methods similar to gravitational wave analytic methodologies, do not depend on multidetector coincidence detection.

Furthermore, certain timeseries analysis and forecasting methods are highly sensitive to the sequence in which events occur. For example, the frequency domain power spectrum of a time series s(t) can accurately establish the probability of the identity of an object when ordinary human and timeseries methods fail to identify the object correctly. The power spectrum of a classical symphony or other musical work reveals in each time segment the dominating key, through the pattern of spectral intensities at frequencies associated with fundamentals and harmonics. If the sections of the musical work are played in a different order, the power spectrum would not change, but the ear and the mind, which perform a time-frequency analysis, perceive a very different content compared to how the original symphony is perceived. Therefore, to avoid excessive sensitivity to arbitrary differences in the sequencing of events, embodiments of the invention rely on frequency-domain power spectrum analysis methods to detect predominant frequencies and motifs.

On a finite segment of length delta-t, the resolution in frequency is 1/delta-t. We can give up fine resolution in frequency space but, by so doing, gain information about when an event happened. Therefore, for some embodiments, rather than working in frequency space with arbitrarily good resolution, we operate in the time-frequency plane, achieving a good compromise between the accuracy in frequency and the accuracy in time. This has advantages when we aim to detect transient phenomena, such as gravitational wave bursts or irregular alternations of patterns of health-care activity (motifs) that arise in conditions that undergo periods of exacerbation and remission, such as multiple sclerosis, lupus, rheumatoid arthritis, and inflammatory bowel disease.

In this regard, it is a commonplace that people naturally experience 'epochs' in their personal health history. Each epoch is associated with characteristic patterns and rates of health services utilization. Relatively frequent utilization of health care is typical of infancy and young childhood, and the rate of utilization decreases for most young adults. For women of child-bearing age, gynecologic exams and treatments follow distinctive patterns in western countries, as do prenatal visits for uncomplicated pregnancy vs. complicated/high-risk pregnancy.

Elective surgeries and their subsequent follow-ups are another kind of 'motif.' The temporal event motifs of chronic conditions like cancer or hepatitis or HIV/AIDS are distinct and different from motifs associated with chronic ambulatory-sensitive conditions such as heart failure, chronic obstructive lung disease, or diabetes. The motifs associated with declining health in the elderly are punctuated by 'ups-and-downs', but the epochs' durations and successors are not, in general, as predictable as for the conditions noted for 'exacerbations-and-remissions'. Through power-spectrum analysis methods, the offset of one epoch and the onset of a new epoch can often be detected from time series, within a span of three or four events, for example.

Turning now to FIG. 1A, an example operating environment 100 suitable for practicing embodiments of the invention is shown. Example operating environment 100 includes a computerized system for compiling and running an embodiment of a decision support recommendation service. With reference to FIG. 1A, a first premise location 110 includes a network behind firewall 150 communicatively coupled to Network 175. Premise location 110, which may comprise separate geographical locations, further includes one or more health record systems such as for example, Hospital Electronic Health Record System 161, Hospital Electronic Health Record System 163, Ambulatory Clinic Electronic Health Record System 165, and Health Information Exchange Electronic Health Record System 167, each communicatively coupled to network 175. In embodiments, Network 175 includes the Internet, a public network, or a private network. Embodiments of health record systems 161, 163, 165, and 167 include one or more data stores of health records and may further include one or more computers or servers that facilitate the storing and retrieval of the health records. Embodiments of health record systems 161, 163, 165, and 167 may further comprise a local or distributed network, which can include network 175, in some embodiments. Firewall 150 may comprise a separate firewall associated with each health record system, in some embodiments. Furthermore, in some embodiments, one or more of the health record systems may be located in the cloud or may be stored in data stores that are distributed across multiple physical locations. In some embodiments, one or more health record systems are communicatively coupled to the cloud, which may include or be communicatively coupled to network 175. In some embodiments, health record systems include record systems that store real-time or near real-time patient information, such as wearable, bedside, or in-home patient monitors, for example.

Example operating environment 100 further includes computer system 120, which may take the form of a server, within premise 130, which is communicatively coupled through firewall 152 and network 175 to health record systems 161, 163, 165 and 167 in premise location 110, and also to linkage manager 140. In embodiments, linkage manager 140 may take the form of a software application operating on one or more mobile computing devices, tablets, smartphones, front-end terminals in communication with back-end computing systems terminals, laptops or other computing devices. In some embodiments, linkage manager 140 includes a web-based application or collection of applications that is usable to manage services provided by embodiments of the invention. In some embodiments, manager 140 comprises a Master Patient Index (MPI) manager and/or a Pseudo-MPI manager application.

Figure 1B:
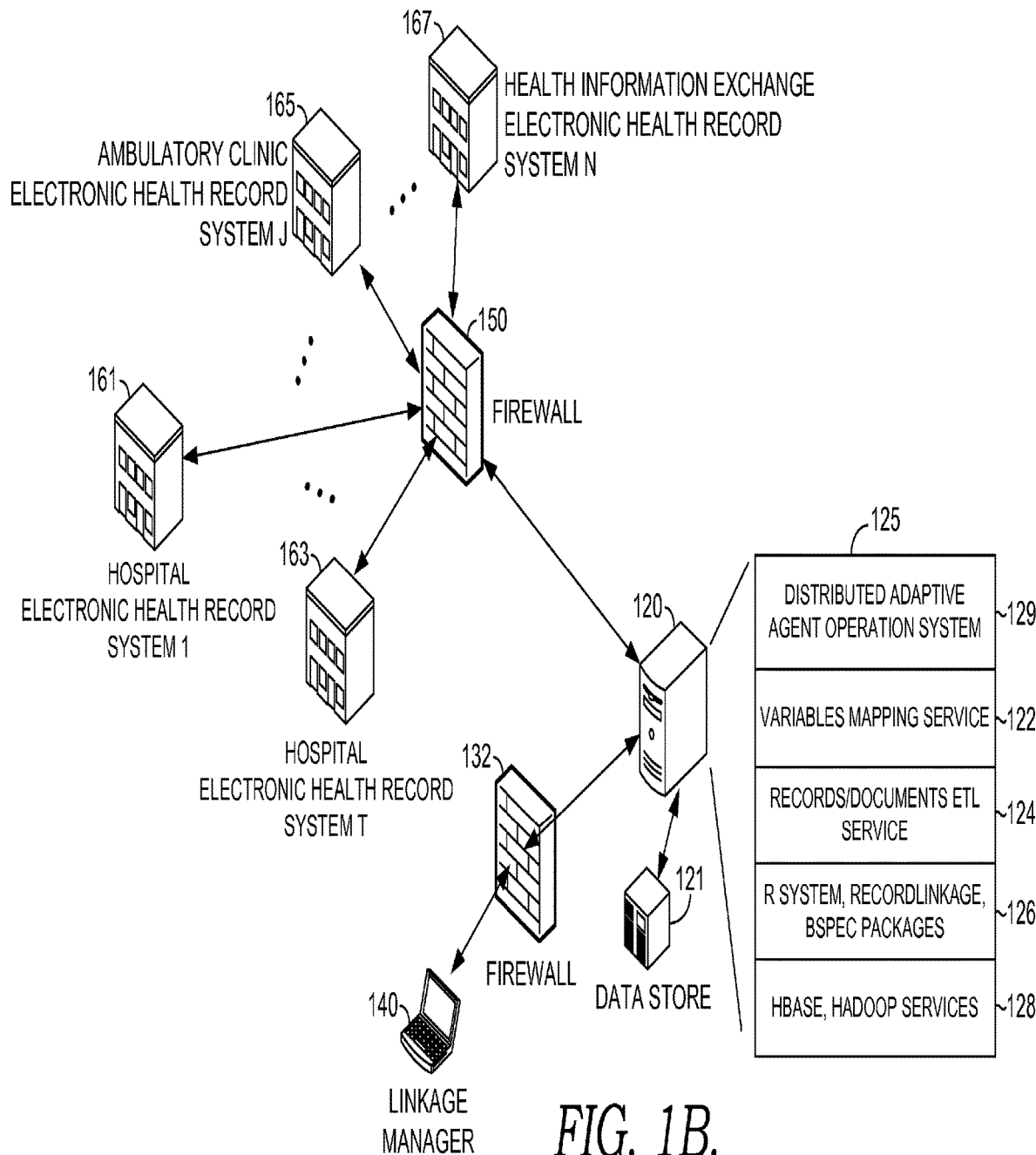

Embodiments of computer software stack 125 run on a computer system such as 120 shown in FIGS. 1A and 1B. Embodiments of software stack 125 may run as a distributed system on a virtualization layer within computer system 120. Embodiments of software stack 125 include a distributed adaptive agent operating system 129 that can host a number of services such as 122, 124, 126, and 128. Embodiments of services 122, 124, 126 and 128 run as a local or distributed stack on a collection of personal computers and servers such as 120 and/or a computing device supporting linkage manager 140. In one embodiment, manager 140 operates in conjunction with software stack 125. In embodiments, variables mapping service 122 and records/documents ETL service 124 provide services that facilitate retrieving frequent item sets, extracting database records, and cleaning the values of variables in records. Software packages 126 perform statistical software operations, and include statistical calculation packages such as, in one embodiment, the R system and R-system modules, and packages such as RecordLinkage and bspec for facilitating calculation of Bayesian power spectra or related statistical analyses for time series data. An example embodiment employing software packages 126 is described in connection to FIG. 2, wherein a RecordLinkage package is associated with the steps at 240 and bspec is associated with steps at 230. Software packages 126 are associated with some embodiments of services 128. Embodiments of services 128 can include Apache Hadoop and Hbase framework that provide a distributed file system.

FIG. 1B illustratively depicts another aspect of an example operating environment. Some of the components of FIG. 1B are described above with respect to FIG. 1A. Also shown in FIG. 1B is data store 121, which in some embodiments includes patient data and information for multiple patients; variables associated with recommendations; recommendation knowledge base; recommendation rules; recommendations; recommendation update statistics; operational data store, which stores events; frequent itemsets (such as "X often happens with Y," for example) and itemsets index information; association rulebases, agent libraries, and other information, patient-derived data, and health-care provider information, for example. Although depicted as a single data store, data store 121 may comprise more than one data store one or multiple locations, or in the cloud. The example operating environment of FIG. 1B also includes a firewall 132 between manager 140 and computer system 120.

Figure 1C:
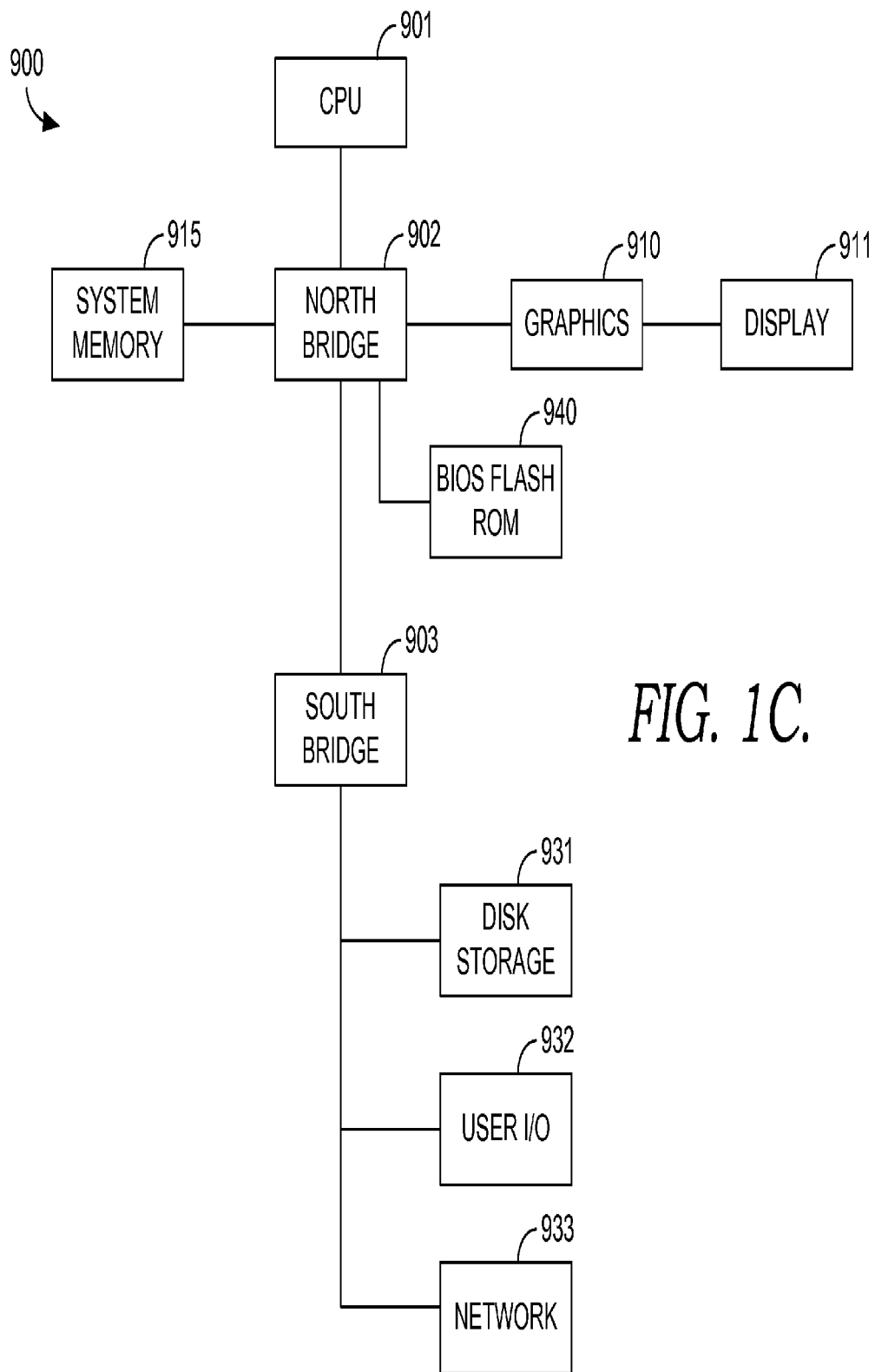

Turning now to FIG. 1C, there is shown one example of an embodiment of computer system 900 that has software instructions for storage of data and programs in computer readable media. Computer system 900 is representative of a system architecture that could be used for computer systems such as 120 and the computer device(s) operating manager 140. One or more CPU's such as 901 have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north bridge device 902 allowing CPU 901 to store instructions and data elements in disk storage 931 such as a fixed disk or USB disk, or to make use of network 933 for remote storage. User I/O device 932, such as a communication device, a mouse, a touch screen, a joystick, a touch stick, a trackball, or keyboard, couples to CPU through south bridge 903 as well.

In some embodiments, computer system 900 is a computing system made up of one or more computing devices. In an embodiment, computer system 900 includes an adaptive multiagent operating system, but it will be appreciated that computer system 900 may also take the form of an adaptive single agent system or a nonagent system. Computer system 900 may be a distributed computing system, a centralized computing system, a single computer such as a desktop or laptop computer, or a networked computing system.

In some embodiments, computer system 900 is a multi-agent computer system. A multiagent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities, and choices that communicate via declarative messaging and use abstractions to allow for future adaptations and flexibility. An agent has its own thread of control, which promotes the concept of autonomy. Additional information about the capabilities and functionality of agents and distributed multiagent operating systems, as they relate to these embodiments, is provided in U.S. patent application Ser. No. 13/250,072, filed on Sep. 30, 2011, which is herein incorporated by reference in its entirety.

Figure 4:
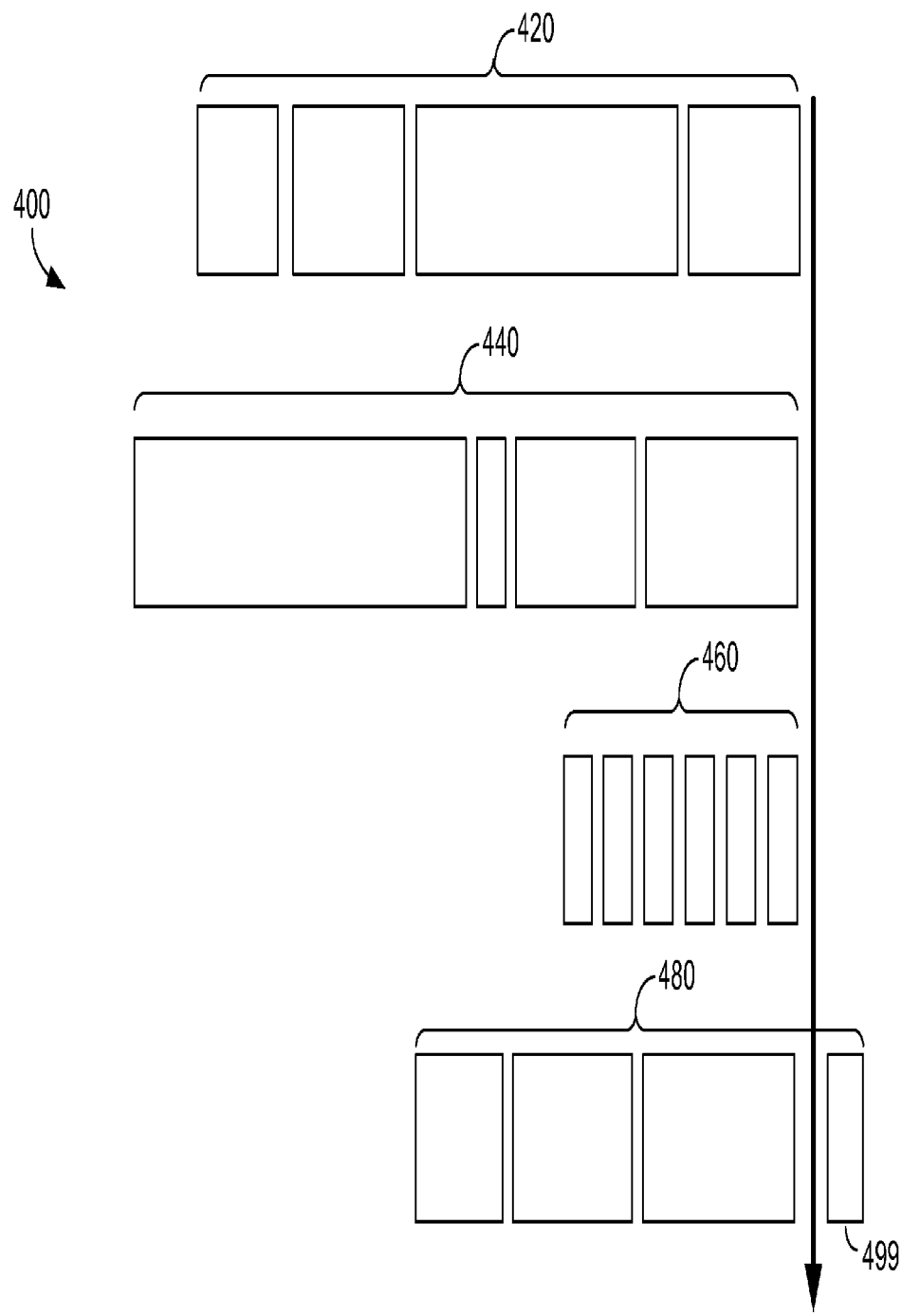
FIG. 4 depicts an illustrative representation of an embodiment for generating a set of plausible record linkages.

Turning now to FIG. 4, an illustrative representation of an embodiment for generating a set of plausible record linkages is depicted, and generally referred to herein as 400. In the embodiment illustratively depicted in 400, patient data concerning "epochs" (e.g., sets of three- or four-visit episodes of patient care associated with characteristic patterns or rates of health service utilization) or other available sets of information about patient care episodes is accessed. Bars 420, 440, 460, and 480 represent serial episodes for four separate candidate cases for matching. For each candidate match, recent encounters and date-time coordinates of each encounter are accessed or determined, from available health records, and sorted in chronological order. It cannot be assumed, that at any given moment, each available health record system necessarily has received all of the updates concerning a patient in a timely or synchronous way. Some data about a patient may have been entered later in time, or not entered in a chronological order. For example, a health information exchange system in a particular state may have data about a patient that slowly trickles in due to administrative burdens for entering patient data. Thus, embodiments contemplate and account for the possibility that certain pieces of patient data may be leading or lagging each other in time.

Next, the current episode or record's date-time coordinates are inserted or appended to the most recent episode for current match-candidate cases. Embodiments of a date-time coordinate, or date-time information, can include date information, time information, or both date and time information. In some embodiments, candidate cases may be limited to patient cases that are determined to be a possible match by comparing other patient data variables, such as patient names, birth dates or age, gender, or similar variables that may be used to determine possible, but not necessarily determinative, matches. The time difference ("delta-t") between serial encounters is then determined and assembled as a time series. Accordingly in embodiments, each time series represents a time difference between encounters. For example, a single time series vector may comprise 4 elements, each element representing the number of days since the previous health-care visit by a patient who is a match candidate. In some embodiments, the time series is cast as an R datatype, for the R package, as described in connection to packages 126 of FIGS. 1A and 1B.

Next, a power spectra for each time series is calculated. The likelihood of the spectra are then determined. In some embodiments, this is facilitated by permuting each spectrum multiple times using Bayesian Chain Monte Carlo simulation, from which a central tendency or median likelihood is determined. In some embodiments, a stable result is determined from performing at least 500 iterations.

In some embodiments, in conjunction or in addition to the above steps, a record linkage scoring weight is also determined by, for example, performing record linkage calculations based on demographic variables such as census-type and slow-moving variables such as age, gender, and race. Further, in some embodiments, F-S methods are used to determine this record-linkage weight.

In embodiments where a record linkage scoring weight is also determined, it is then combined with the power spectrum median weight, by for example RMS calculation or similar method for measuring distances such as, for example, cosine or correlation coefficient. The results of this combination are ranked, and the threshold is used to identify a positive (correct) match, shown as 499 in the example of FIG. 4. In embodiments, this threshold may be set based on the specific purpose of use. For example, a higher threshold may be in order in individual care scenario where significant harm would result from an improper match. Similarly, lower thresholds may be set for scenarios unlikely to result in significant harm to a patient, such as epidemiological purposes.

Turning back to FIG. 2, a flow diagram is provided, which depicts an embodiment of a method for generating a set of plausible record matches, and which is generally referred to herein as 200. At a step 205, bind the current entity of interest. In embodiments, the entity of interest represents the record of a person or object for which candidate matches are sought. In some embodiments, method 200 may be used for matching objects, items, or data sets rather than people, such as, inventoried equipment matching, matching objects associated with data entries, or data sets such as certain patterns of transactions, travel, or behavior. At a step 210, index hash values are calculated for blocking variables. Blocking variables can include variables such as birthday, birth month, birth year, or may also include variables in a specific context, such as whether the patient is a kidney patient, whether the patient is on dialysis, has or had prostate cancer, or is diabetic, for example. In some embodiments, blocking variables may be used to determine how data sets are retrieved, when dealing with large-demographic data sets. Continuing with step 210, a plurality of independent demographic variables that are present in both a reference system and a target system associated with each entity, are selected to be used as blocking variables.

At a step 215, for each M blocking variable, N instances are extracted to constitute a candidate matching table, where M and N are integers greater than or equal to zero. More specifically, from the target system, extract those database records containing lexically similar values for the selected blocking variables' values. In some embodiments, this step is facilitated using a hash table to establish the degree of similarity for retrieval.

At a step 220, for each database entity retrieved, extract the date-time coordinates for the episodes that the retrieved records represent; compute interepisode time intervals that separate the records in time; and assemble the intervals as time series associated with each record. In some embodiments, this time series comprises elements representing the time interval between episodes. For example, an example time series might include 5 numbers, each number representing the number of days or hours between episodes. Continuing with step 220, take the date-time coordinate associated with a candidate record to be matched and compute for each retrieved record the time interval that separates the candidate record from date-time stamp of the retrieved entity's most recent record.

Following step 220, steps of method 200 proceed in two paths: steps related to determining Bayesian Power Spectra ("bspec") weights 230, which include steps 232, 234, 236, and 238, and steps related to determining RecordLinkage weights 240, which include steps 242, 244, and 246. In embodiments, steps included in 230 and 240 occur in parallel or sequentially. In some embodiments, agents of a distributive adaptive agent operating system are dispatched to facilitate handling 230, 240 or both. In some embodiments, agents may invoke other agents, as described above in connection to FIG. 1C. For example, a bspec agent might facilitate steps 232-238, and might invoke a second agent for the Bayesian power spectra calculations of step 234, and a third agent for the sorting and ranking in step 236.

Figure 2:
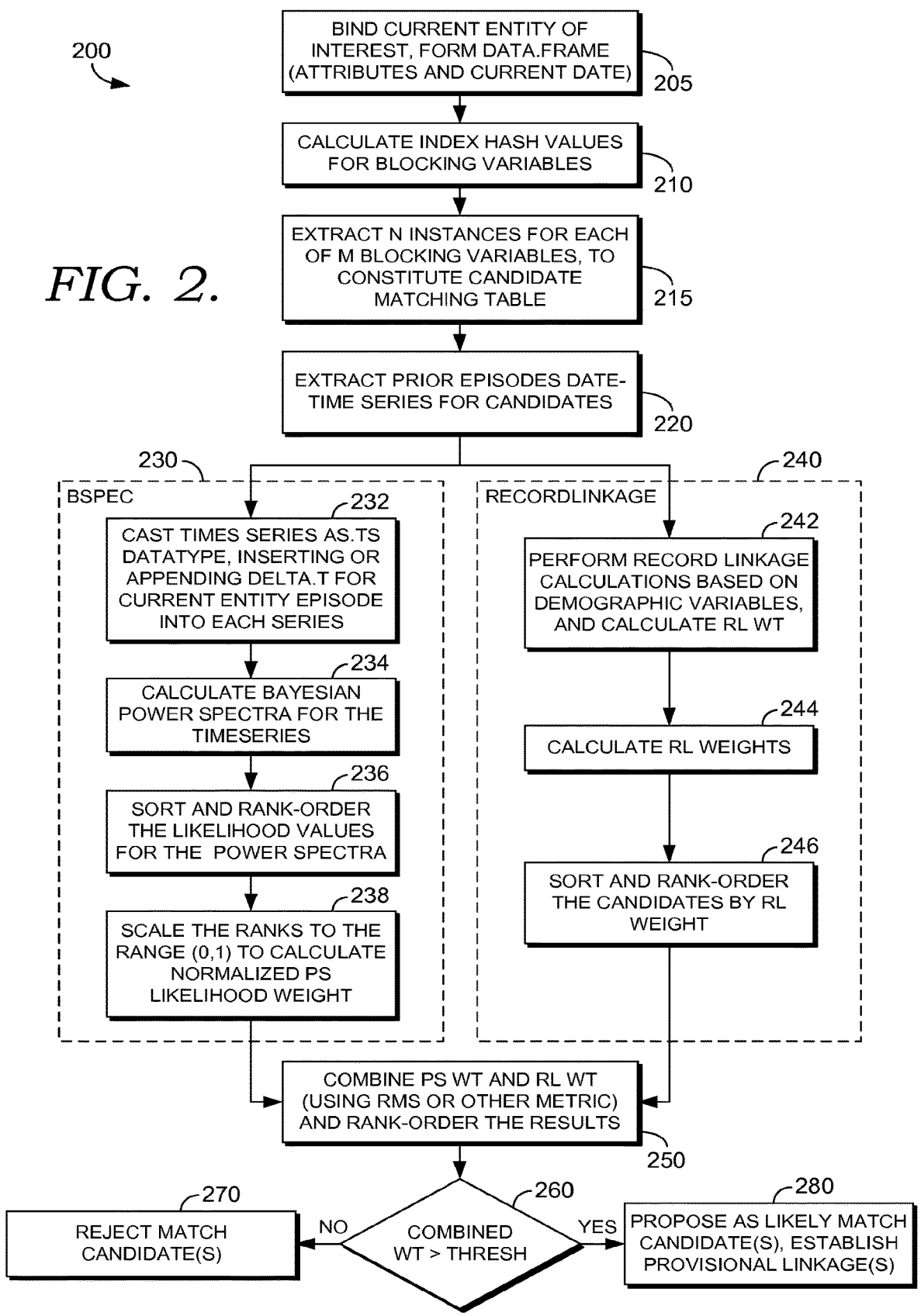
FIG. 2 depicts a flow diagram of an embodiment of a method for generating a set of plausible record matches.

Continuing with FIG. 2, at a step 232, append the time interval as determined in step 220 to the time series for each retrieved entity. In some embodiments, the time series is cast as an R datatype, such as for example ".ts," for the R package, as described above in connection to packages 126 of FIGS. 1A and 1B. At a step 234, determine the power spectra for each time series from step 232. In some embodiments, the power spectra may be calculated on only a portion of the time series from step 232. For example, in embodiments, certain time series may be excluded based on the values of the elements, such as elements representing zero days between episodes, or negative or unusually high values, which might represent an error. Continuing with step 234, calculate the likelihood (probability) of each determined spectrum. In some embodiments, the likelihood of each spectrum is determined by iteratively permuting the spectrum and sampling the resulting permutations by Bayesian Markov Chain Monte Carlo simulation. In some embodiments, this simulation is performed for at least 500 iterations, retaining the median likelihood for each entity, to obtain a stable result.

At a step 236, median likelihood values determined in step 234 are sorted and ranked. At a step 238, the likelihood values are normalized to form a power spectrum weight ("PS_wt") for each entity. For example, in some embodiments, the likelihood values are normalized to lie within the range (0,1).

Turning now to the steps for determining RecordLinkage weight 240, at steps 242 and 244, determine record linkage weight for each entity. In some embodiments, perform record linkage calculations on candidate record and the retrieved records, retaining for each a measure of numerical lexical similarity. In some embodiments, this may be facilitated by epiWeight or similar methods to form a record linkage weight (RL_wt) for each entity. In some embodiments, an opensource R recordlinkage software package may be used to facilitate forming a record linkage weight for each entity. In some embodiments, record linkage calculations are based on demographic variables, such as for example, slow-moving variables or census-type variables. At a step 246, candidate matches are sorted and ranked by RL_wt.

At a step 250, power spectrum weights from steps associated with 230 and record linkage weights from steps associated with 240 are combined to form a composite score. In some embodiments, the weights are combined by root-mean-square (RMS), cosine transform, correlation coefficient, or other similar means. In some embodiments, the combined weight is rank-ordered.

In some embodiments median power spectrum likelihood determination from steps associated with 230, such as ascertained by Bayesian Markov Chain Monte Carlo simulation, may be treated as one biomarker or 'weight' that measures the similarity of a record associated with the current entity to records from putative matching entities stored in the target database. Likewise, in steps associated with 240, a weight denoting degree of similarity that is calculated by record linkage methods, which may include those using F-S may be considered another biomarker. Furthermore, in some embodiments, where it may be difficult to find single biomarkers that perform with adequate accuracy, panels of biomarkers may be used such that a plurality of marker values is combined. In some embodiments, this is facilitated using linear combinations or decision-tree rule induction.

At a step 260, determine for the entity whether the composite weight score exceeds a threshold. In some embodiments, the threshold is a heuristic threshold. In some embodiments, the use case associated with the record linkage is used to determine the threshold. For example, in an epidemiological use, a lower threshold may be appropriate, but for individual care, where significant harm could result from a mistaken record linkage, a higher threshold may be used. In some embodiments, a health-care provider may set the threshold; the threshold may be set from a table of associated use cases for record linkages; or the threshold may be set based on the determined combined weights, for example, where there is a gap between successive rank-ordered combined weights. In some embodiments, an agent of a multiagent computer system, such as 120 of FIGS. 1A and 1, is used to set the threshold.

At a step 270, entities having a composite score falling below the threshold are rejected as an improbable match that should not be linked with the candidate record. At a step 280, candidates with combined weights falling above the threshold are proposed as likely match candidates that merit consideration for linkage. In some embodiments, provisional linkages are audited before merging; for example, a health-care provider or trained individual might review and confirm patient matches. In some embodiments, linkages may be determined as "pseudo-linkages" or linkages that are identified as probably matches without actually merging the records. These linkages may be used in certain use cases such as, for example, epidemiological studies. In some embodiments, use cases, such as certain epidemiological studies or other use cases, such as for example population research may use persisting pseudo-linkages, which preserve provisional linkages.

FIG. 3 provides an example output of an embodiment for resolving an entity and determining provisional linkage. In the example embodiment used in connection to FIG. 3, an entity resolver subsystem was reduced to practice using a server cluster running the Linux operating system, the open-source statistical software package R, and R modules bspec and RecordLinkage.

Records were randomly selected from a data warehouse, such as Cerner Health Facts®, which is derived from electronic health record (EHR) from 100% of episodes of care that are incident upon more than 130 U.S. based institutions. In this example, personally identifiable information is removed in conformance with U.S. HIPAA law and regulations, and the de-identified data is stored in a separate, secure database. From a total of 50,000 encounters between 1 Jan. 2006 and 1 May 2011, a subset of 13,392 patients were identified who had three or more episodes during this time frame. An unrelated synthetic dataset of 10,000 names and birth dates was obtained.

Application of this embodiment using this data was able to correctly resolve 100% of the true linkages between example candidate records and the merged synthetic dataset, and exhibited 0% false-positive and 0.2% false-negative classifications.

Turning to FIG. 3, table 300 shows rows, including row 332, row 334, and rows 340 of candidate matches. Column variables 303 and 305 were supplied by the data warehouse. Variables 303 include patient-name related information and birth year (by), birth month (bm), and birthday (bd). Variables 305 (columns v1 through v4) are days between visits, where a candidate patient or entity that may be linked with a reference record is shown in each row. In other words, if a current patient named "Michael Meyer" is visiting today and is to be linked with the MICHAEL MEYER record shown in the first row 332, then today's date (for visit #4) would be 187 days subsequent to the previous (v3) visit for that individual, which in turn was 168 days subsequent to the immediately prior visit (v2), and so on. Similarly, from today's date, it has been 60 days since Michael Myer (no "e") was last seen, as shown column v4 of row 334. In this example, the first row might represent regular doctor check-ups or routine visits, since the days are spread apart. The second row might represent a treatment because the time interval between visits is smaller.

In this example embodiment, values v1 through v4 for each row form a time series, with each time series comprising a vector with 4 elements (the values of v1, v2, v3, and v4). From the time series vectors, a Bayesian power spectrum weight (ps_wt) is determined for each entity row, as described above in connection to FIG. 2 and shown in column 309. Similarly, for each entity, a record linkage weight (rl_wt), shown in column 307, is determined for each row. Column 310 shows a combined composite weight of the rl_wt and ps_wt. In this example embodiment, RMS is used to determine the composite weight or score. Furthermore, here the scores are normalized to (0,1).

In this example, a threshold 320 is set at 0.75, indicating that the first two rows 332 and 334, which have composite scores (column 310) greater than the 0.75 threshold value, are true positive (i.e., correct) linkages. Remaining rows 340 represent the 18 nearest matches, out of the nearly 10,000 record test dataset. In this example embodiment, threshold 320 is determined by specificity and sensitivity. Here, sensitivity is set to 100% and specificity is set to 99.98%.

(Entity linkage prevalence is equal to 0.12%.) These values are appropriate for use cases of individual patient care, where significant harm might occur due to a mistaken linkage. For epidemiological (or similar) purposes, specificity might equal 80%, and sensitivity might equal 95%.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the claims.

Some embodiments of the present invention include methods and computer-readable media having computer-executable instructions embodied thereon for performing a method of identifying related records in a data store comprised of a plurality of records, the method comprising steps of: retrieving for each record a linkage indicator variable denoting whether the record is associated with one or more records for the individual or the same identity in the database; retrieving date-time information associated with each episode record; identifying blocking variables and using record linkage to create a subset of plausibly related records from the records in the data store; determining a power spectra likelihood weight for each record in the subset; determining a record linkage weight for each record in the subset; determining a composite score by combining the power spectra likelihood weight and record linkage weight; comparing the composite score to a threshold value; and if the composite score is greater than the threshold value, identifying a record as a related record, but if the composite score is less than the threshold, identifying the record as not related.

Some embodiments of the present invention include methods and computer-readable media having computer-executable instructions embodied thereon for performing a method of identifying related records in a data store comprised of a plurality of records, the method comprising steps of: assigning a unique identifier to all records in the database that do not already have a unique identifier, the records arranged in rows and columns; retrieving for each record the linkage indicator variable denoting whether the record is associated with one or more records for the individual or the same identity in the database; retrieving the date-time stamps associated with each episode record; creating a blocking subset by conventional record linkage methods of between 1 and all of the columns in the database; creating a subset (s) consisting of the unique identifiers of records (r) from the database wherein the composite score combining the evidence from a record similarity measure and a power spectrum likelihood measure is greater than or equal to a heuristic value wherein the heuristic value is a positive real number, m; and outputting the unique identifiers of record matches identified by the pair-wise matching algorithm.

In some embodiments, a subset is not utilized, and a power spectra weight and record linkage weight are determined for each record in the record store. In some embodiments, the subset includes records for which episode-information comprising at least 3 visits or date-time entries is present.

Some embodiments further include wherein applying a pair-wise matching algorithm step further comprises matching a candidate record X against records in the database. Some embodiments further include wherein the blocking subset of records has record linkage coefficients or weights computed, according to one of the methods are commonly practiced by those experienced in the art, and the subset (s') of records whose weights exceed an heuristic value (RL_wt) is derived. Some embodiments further include wherein the most recent date-time coordinate of each record for the plurality of episodes Y in subset s' is subtracted from the date-time coordinate for the candidate record X to calculate a time difference, and this difference is appended to the time series of Y where the length of each such time series comprises not less than 4 time intervals.

Some embodiments further include wherein the time series comprises time intervals separating the episodes that are associated with the plurality of records are used to calculate a set of frequency-domain power spectra. Some embodiments further include wherein the power spectra are subjected to repeated random permutations of the spectral frequencies, determine a median likelihood for each entity. Some embodiments further include wherein the probabilistic likelihoods for the power spectra are computed by Bayesian Markov Chain Monte Carlo sampling.

Some embodiments further include wherein the set of likelihood values are sorted and rank-ordered, and some of the embodiments further include wherein the ranks of the likelihoods are scaled by arithmetic means such that the scaled values are in the range (0,1) to produce a power spectrum weight (PS_wt) for each record.

Some embodiments further include wherein the record linkage weight and power spectra weight values are combined by a root-mean-square transformation, cosine transformation, or other suitable means of combining multiple numerical indices of similarity or lexical closeness, and the resulting score is associated with each record. Further, some embodiments include wherein the elements of this associated resulting score are sorted in decreasing score order.

What is claimed:

1. A computer-implemented method comprising:
  receiving a target record from a first record system, the target record comprising one or more first date-time variables associated with a target patient, wherein each of the one or more first date-time variables identifies a date and/or time;
  receiving a candidate record from a second record system, the candidate record comprising a second date-time variable for an episode associated with the target patient, wherein the second date-time variable identifies a date and/or time;
  generating an interim record that aggregates the first date-time variables with the second date-time-variable;
  generating a power spectrum based on the interim record;
  predicting, based on at least one demographic characteristic of a subject, a record linkage weight based on a similarity of a demographic variable associated with the candidate record and the target record;

determining, based on the record linkage weight and the power spectrum, that the candidate record is related to the target record; and storing an indication that the candidate record is to be linked to the target record.

2. The computer-implemented method of claim 1, further comprising:

determining a power spectra weight based on a characteristic of the power spectrum and a corresponding reference characteristic generated using a set of reference power spectra, wherein determining that the candidate record is related to the target record is based on the record linkage weight and the power spectra weight.

3. The computer-implemented method of claim 2, further comprising:

determining a composite weight of the record linkage weight and the power spectra weight, wherein determining that the candidate record is related to the target record comprises determining that the composite weight satisfies a threshold.

4. The computer-implemented method of claim 2, wherein determining the power spectra weight comprises:

determining a likelihood value of each spectrum of the set of reference power spectra; and normalizing the determined likelihood values.

5. The computer-implemented method of claim 2, wherein the set of reference power spectra are generated using a Bayesian Markov Chain Monte Carlo simulation.

6. The computer-implemented method of claim 1, wherein the second date-time variable comprises a date-time value associated with a most recent episode stored in association with the candidate record.

7. The computer-implemented method of claim 1, wherein the first and second record systems comprise the same record system.

8. The computer-implemented method of claim 1, further comprising:

presenting, via an interface, an indication that the candidate record is related to the target record.

9. A system comprising:

one or more data processors; and a non-transitory computer readable storage medium containing instructions which, when executed on the one or more data processors, cause the one or more data processors to perform a set of actions including:

receiving a target record from a first record system, the target record comprising one or more first date-time variables associated with a target patient, wherein each of the one or more first date-time variables identifies a date and/or time;

receiving a candidate record from a second record system, the candidate record comprising a second date-time variable for an episode associated with the target patient, wherein the second date-time variable identifies a date and/or time;

generating an interim record that aggregates the first date-time variables with the second date-time-variable;

generating a power spectrum based on the interim record;

predicting, based on at least one demographic characteristic of a subject, a record linkage weight based on a similarity of a demographic variable associated with the candidate record and the target record;

determining, based on the record linkage weight and the power spectrum, that the candidate record is related to the target record; and storing an indication that the candidate record is to be linked to the target record.

10. The system of claim 9, wherein the set of actions further includes:

determining a power spectra weight based on a characteristic of the power spectrum and a corresponding reference characteristic generated using a set of reference power spectra, wherein determining that the candidate record is related to the target record is based on the record linkage weight and the power spectra weight.

11. The system of claim 10, wherein the set of actions further includes:

determining a composite weight of the record linkage weight and the power spectra weight, wherein determining that the candidate record is related to the target record comprises determining that the composite weight satisfies a threshold.

12. The system of claim 10, wherein determining the power spectra weight comprises:

determining a likelihood value of each spectrum of the set of reference power spectra; and normalizing the determined likelihood values.

13. The system of claim 10, wherein the set of reference power spectra are generated by sampling permutations of the power spectrum.

14. The system of claim 9, wherein the second date-time variable comprises a date-time value associated with a most recent episode stored in association with the candidate record.

15. The system of claim 9, wherein the first and second record systems comprise the same record system.

16. The system of claim 9, wherein the set of actions further includes:

presenting, via an interface, an indication that the candidate record is related to the target record.

17. A computer-program product tangibly embodied in a non-transitory machine-readable storage medium, including instructions configured to cause one or more data processors to perform a set of actions including:

receiving a target record from a first record system, the target record comprising one or more first date-time variables associated with a target patient, wherein each of the one or more first date-time variables identifies a date and/or time;

receiving a candidate record from a second record system, the candidate record comprising a second date-time variable for an episode associated with the target patient, wherein the second date-time variable identifies a date and/or time;

generating an interim record that aggregates the first date-time variables with the second date-time-variable;

generating a power spectrum based on the interim record;

predicting, based on at least one demographic characteristic of a subject, a record linkage weight based on a similarity of a demographic variable associated with the candidate record and the target record;

determining, based on the record linkage weight and the power spectrum, that the candidate record is related to the target record; and storing an indication that the candidate record is to be linked to the target record.

18. The computer-program product of claim 17, wherein the set of actions further includes:

determining a power spectra weight based on a characteristic of the power spectrum and a corresponding reference characteristic generated using a set of reference power spectra, wherein determining that the candidate record is related to the target record is based on the record linkage weight and the power spectra weight.

19. The computer-program product of claim 18, wherein the set of actions further includes:
determining a composite weight of the record linkage weight and the power spectra weight, wherein determining that the candidate record is related to the target record comprises determining that the composite weight satisfies a threshold.

20. The computer-program product of claim 18, wherein determining the power spectra weight comprises:
determining a likelihood value of each spectrum of the set of reference power spectra; and
normalizing the determined likelihood values.

* * * * *